United States Patent [19]

Howard, Jr.

[11] Patent Number: 5,147,881

[45] Date of Patent: Sep. 15, 1992

[54] 4-(1,2-BENZISOXAZOLYL)PIPERIDINE ANTIPSYCHOTIC AGENTS

[75] Inventor: Harry R. Howard, Jr., Groton, Conn.

[73] Assignee: Pfizer Inc, New York, N.Y.

[21] Appl. No.: 612,776

[22] Filed: Nov. 14, 1990

[51] Int. Cl.[5] ............... A61K 31/445; C07D 413/14
[52] U.S. Cl. ................. 514/321; 546/198; 546/201
[58] Field of Search ............ 546/198; 514/321

[56] References Cited

U.S. PATENT DOCUMENTS

| | | | |
|---|---|---|---|
| 4,458,076 | 7/1984 | Strupczewski | 546/198 |
| 4,558,060 | 12/1985 | Caignard et al. | 514/375 |
| 4,831,031 | 5/1989 | Lowe et al. | 514/254 |

FOREIGN PATENT DOCUMENTS

| | | | |
|---|---|---|---|
| 196132 | 10/1986 | European Pat. Off. | |
| 2621588 | 4/1989 | France | 546/198 |

OTHER PUBLICATIONS

Strupezewski et al., "Synthesis of and Neuroleptic . . . ", J. Med. Chem., 28, 761–769 (1985).

*Primary Examiner*—C. Warren Ivy
*Assistant Examiner*—Celia Chang
*Attorney, Agent, or Firm*—Peter C. Richardson; J. Trevor Lumb; Gregg C. Benson

[57] ABSTRACT

Certain 1-substituted 4-(1,2-benzisoxazolyl)piperidine compounds exhibit neuroleptic activity and are useful in the treatment of psychosis and anxiety.

7 Claims, No Drawings

4-(1,2-BENZISOXAZOLYL)PIPERIDINE ANTIPSYCHOTIC AGENTS

BACKGROUND OF THE INVENTION

The present invention is directed to novel 1-substituted 4-(1,2-benzisoxazolyl)piperidine compounds which exhibit neuroleptic activity and are useful in the treatment of psychosis and anxiety.

Other compounds useful in treating psychotic disorders are known. For example, U.S. Pat. Nos. 4,558,060 and 4,831,031 describe arylpiperazinyl-ethyl or butyl heterocyclic compounds and their use in the treatment of psychiatric disorders. European Patent Application 0196132 teaches 1,2-benzisoxazol-3-yl and 1,2-benzisothiazol-3-yl derivatives useful in treating psychiatric disorders.

Although the above compounds have been discovered, there is a continual search in this field of art for other more effective compounds.

SUMMARY OF THE INVENTION

This invention is directed to 1-substituted 4-(1,2-Benzisoxazolyl)-piperidine compounds that are useful in the treatment of psychosis and anxiety. The compounds of this invention have the formula

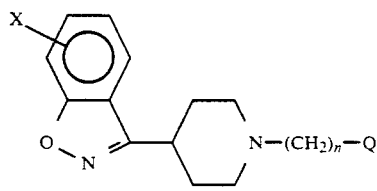

Formula I and the pharmaceutically acceptable base salts thereof; wherein
X is H, halo, $C_1$-$C_4$ alkyl, $C_1$-$C_4$ alkoxyl or $CF_3$;
n is 2, 3 or 4; and
Q is

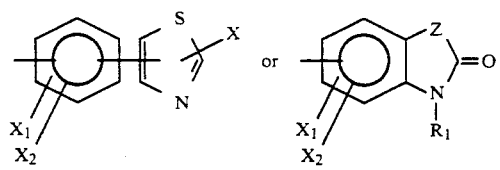

wherein Z is $CR_2R_3$, $CR_2R_3CR_4R_5$, $CR_2R_3CR_4R_5CR_6R_7$, O or S; $R_1$, $R_2$, $R_3$, $R_4$, $R_5$, $R_6$ and $R_7$ are H, or $C_1$-$C_4$ alkyl; and $X_1$ and $X_2$ are H or halo. Solvates (e.g. hydrates) of the above compounds are also included within the scope of the definition of formula I.

Particularly preferred compounds are compounds of formula I wherein Z is $CR_2R_3$ or $CR_2R_3CR_4R_5$. Preferred within this group are compounds where n is 2 and X is H or halo. Preferred within this group are compounds where X is halo, $X_1$ and $X_2$ are H, and $R_1$, $R_2$, $R_3$, $R_4$ and $R_5$ are H or methyl.

A second preferred group of compounds of formula I are those wherein Q is phenyl substituted with thiazolyl, said thiazolyl substituted with X. Preferred within this group are compounds wherein n is 4 and X is H, halo, or $C_1$-$C_4$ alkyl. A preferred compound within this group is 1-(4-(4-(2-methylthiazol-4-yl)phenyl)butyl)-4-(6-fluoro-1,2-benzisoxazol-3-yl)piperidine.

Other preferred compounds are 5-(2-(4-(6-Fluoro-1,2-benzisoxazol-3-yl)-1-piperidinyl)ethyloxindole, 1,3-dimethyl-5-(2-(4-(6-fluoro-1,2-benzisoxazol-3-yl)-piperidinylethyl)oxindole, 3,3-dimethyl-5-(2-(4-(6-fluoro-1,2-benzisoxazol-3-yl)-piperidinyl)ethyl)-oxindole, or 6-(2-(4-(6-fluoro-1,2-benzisoxazol-3-yl)piperidinyl)ethyl)-1,2,3,4-tetrahydro-2(1H)-quinolinone.

The present invention is also directed to pharmaceutical compositions for the treatment or prevention of psychosis and anxiety, which comprises a compound of the formula I and in a pharmaceutically acceptable carrier; and to a method for the treatment or prevention of psychosis or anxiety which comprises administering to a person in need of such treatment or prevention a compound of the formula I in an amount effective to treat or prevent psychosis or anxiety.

Other features and advantages will be apparent from the specification and claims.

DETAILED DESCRIPTION OF THE INVENTION

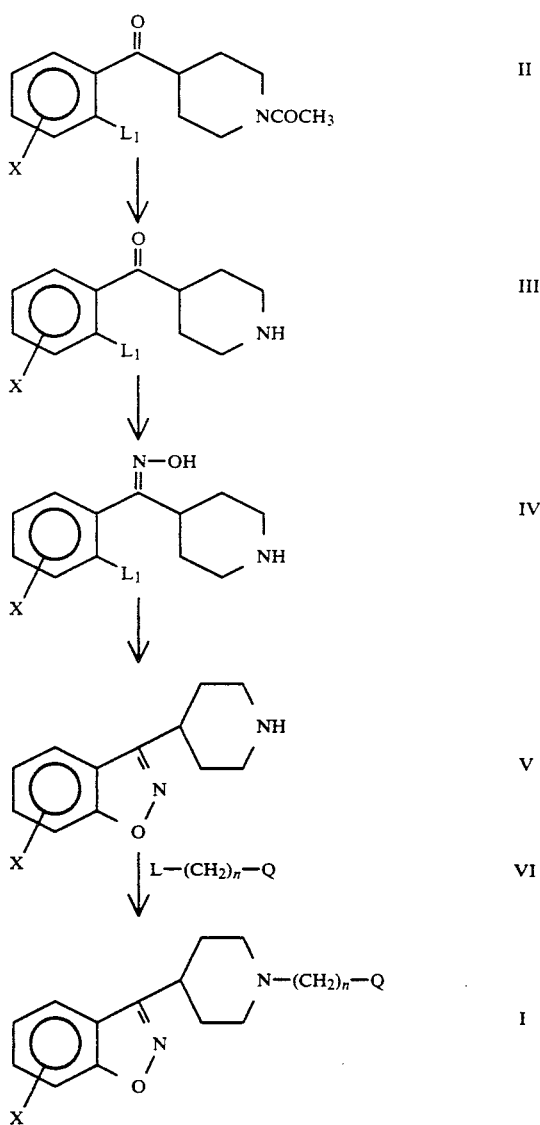

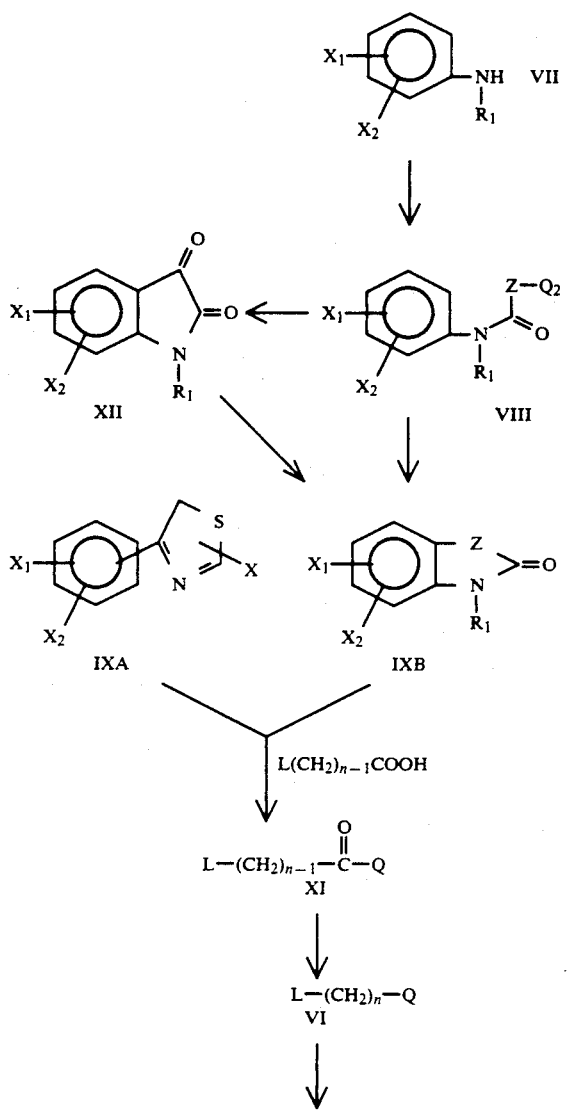

Compounds of the formula I wherein X, n, Q, Z, $X_1$, $X_2$, $R_1$, $R_2$, $R_3$, $R_4$, $R_5$, $R_6$ and $R_7$ are as defined above may be prepared by reacting the appropriate formula V compounds wherein X is as defined above with the appropriate compounds of formula VI wherein X, n, Q, Z, $X_1$, $X_2$, $R_1$, $R_2$, $R_3$, $R_4$, $R_5$, $R_6$ and $R_7$ are as defined above and L is a halogen (e.g. F, Br, Cl, I) or other suitable leaving group (e.g. $CH_3SO_3$, p-toluenesulfonyloxy).

The reaction is generally performed in a polar solvent such as a lower alcohol, dimethylformamide, dimethylacetamide, acetonitrile, or methyl isobutyl ketone, and in the presence of a weak tertiary base such as triethylamine or an inorganic base such as sodium or potassium carbonate. A catalytic amount of sodium or potassium iodide may be employed to further the degree of completion. The reaction may be conducted at a temperature within the range of about 0° C. to about 250° C., and preferably it is conducted at the reflux temperature (boiling point) of the chosen solvent.

The formula V compounds wherein X is as defined above may be made by a modification of a procedure disclosed in European Patent Application publication No. 0196132 described by Kennis et al. Generally a formula IV compound wherein X is as defined above and $L_1$ is a halogen or suitable leaving group is cyclized under basic conditions (e.g. 50% aqueous NaOH) at elevated temperatures of about 30° C. to about 100° C. and preferably at reflux.

The compounds of formula IV wherein X and $L_1$ are as described above may be made by reaction of the appropriate formula III compound wherein X and $L_1$ are as defined above with hydroxylamine hydrochloride and a base such as triethylamine or pyridine, in an inert solvent (e.g., a polar solvent such as a lower alcohol) under reflux conditions in the absence of oxygen.

The compounds of formula III wherein X and $L_1$ are as described above may be made by deacetylation of the appropriate formula II compound, wherein X and $L_1$ are as described above, by heating (e.g., at reflux) in the presence of an acid (e.g., conc. HCl) in the presence or absence of an inert solvent (e.g., acetic acid).

The compounds of formula II wherein X and $L_1$ are as described above may be made by methods known to those skilled in the art, such as by the Friedel Crafts acylation of the appropriately substituted benzene using an N-Acetyl isonipecotoyl halide.

The compounds of formula VI wherein L, X, n, Q, Z, $X_1$, $X_2$, $R_1$, $R_2$, $R_3$, $R_4$, $R_5$, $R_6$ and $R_7$ are as defined above may be prepared by methods available to those practicing in the art and analagous to those described in European Patent Application 0281309. Thus, compounds of the formula VI (described above) may be prepared by reducing the appropriate compound of formula XI wherein L, X, n, Q, Z, $X_1$, $X_2$, $R_1$, $R_2$, $R_3$, $R_4$, $R_5$, $R_6$ and $R_7$ are as defined above, with a reducing agent such as triethylsilane in trifluoroacetic acid.

Compounds of the formula XI wherein L, X, n, Q, Z, $X_1$, $X_2$, $R_1$, $R_2$, $R_3$, $R_4$, $R_5$, $R_6$, and $R_7$ are as defined above may be prepared by reacting the appropriate compound of the formula IXA or IXB wherein X, Z, $X_1$, $X_2$, $R_1$, $R_2$, $R_3$, $R_4$, $R_5$, $R_6$, and $R_7$ are as defined above with a haloalkanoic acid or a haloalkanoyl halide wherein the halogen is selected from the group consisting of Cl, Br and I, employing, for example, Friedel-Crafts conditions (e.g., aluminum trichloride in carbon disulfide or methylene dichloride under an inert atmosphere) or via acylation in a medium such as polyphosphoric acid at a temperature from about room temperature to about 100° C.

Formula Q compounds having the Formula IXA wherein phenyl is substituted with thiazoyl (the thiazolyl is optionally substituted with X as defined above) may be made by standard methods known to those skilled in the art such as described in Preparation E and EP Application 279,548.

Compounds of the formula IXB wherein $X_1$, $X_2$, $R_1$, $R_2$, $R_3$, $R_4$, $R_5$, $R_6$, and $R_7$ are as defined above and Z is $CR_2R_3$, $CR_2R_3CR_4R_5$, $CR_2R_3CR_4R_5CR_6R_7$ may be made by several methods as described in the literature (e.g. U.S. Pat. No. 4,831,031), and outlined above. For example, an aryl amine of formula VII wherein $X_1$, $X_2$ and $R_1$ are as defined above may be converted using methods known in the art, to an arylamide of the formula VIII wherein $X_1$, $X_2$, $R_1$, $R_2$, $R_3$, $R_4$, $R_5$, $R_6$, and $R_7$ are as defined above and $Q_2$ is a leaving group (e.g. halo) which may then be cyclized to produce a compound of the formula IXB.

Alternatively, compounds of formula VIII in which Z is C=O and $Q_2$ is halo (i.e., Cl or Br) may be cyclized (e.g., employing Friedel-Crafts conditions as described above) to a compound of structure XII. These compounds of formula XII may then be reduced to compounds of formula IXB (where $Z=CH_2$) using reduction techniques known to those skilled in the art (e.g., by the Wolff-Kishner reduction, employing hydrazine and a strong base).

Compounds of the formula IXB wherein $X_1$, $X_2$, $R_1$ are as defined above and Z is S or O may be prepared by standard methods known to those skilled in the art (e.g., U.S. Pat. No. 4,831,031). In addition some are commercially available (e.g., 2-Benzoxazolinone is available from Aldrich Chem. Co.)

The pharmaceutically acceptable acid addition salts of the compounds of formula I are prepared in a conventional manner by treating a solution or suspension of the free base, i.e., a compound of formula I, with about one chemical equivalent of a pharmaceutically acceptable acid. Conventional concentration and recrystallization techniques are employed in isolating the salts. Such pharmaceutically acceptable acid addition salts include, but are not limited to the respective salts of acetic, malic, citric, fumaric, sulfuric, hydrochloric, hydrobromic, hydroiodic, sulfonic such as methanesulfonic and p-toluenesulfonic and related acids.

The neuroleptic activity of the present compounds may be demonstrated by methods based on standard procedures. In one method, adult male Sprague-Dawley rats are pretreated with appropriate doses of the test compound by subcutaneous injection. One half hour later all rats are injected intraperitoneally with 1 mg/kg apomorphine hydrochloride dissolved in an 0.1% ascorbate solution. The rats are rated behaviorally according to the following scale at 5, 15, 25, 35 and 45 minutes after the apomorphine injection: 0=alert but not moving, 1=moving around the cage, 2=discontinuous sniffing behavior, 3=continuous sniffing with discontinuous oral movements, and 4=continuous licking and chewing movements.

The neuroleptic activity of the compounds of this invention makes them useful for treating psychotic disorders in human subjects. For example, these compounds are useful for treating psychotic disorders of the schizophrenic types and in particular the compounds are useful for removing or ameliorating such symptoms as anxiety, agitation, excessive agression, tension and social or emotional withdrawal in psychotic patients.

A neuroleptic compound of the formula I or a pharmaceutically-acceptable salt thereof can be administered to a human subject either alone or preferably in combination with pharmaceutically-acceptable carriers or diluents in a pharmaceutical composition according to standard pharmaceutical practice. A compound can be administered orally or parenterally. Parenteral administration includes especially intravenous and intramuscular administration. Additionally, in a pharmaceutical composition comprising a compound of formula I or a pharmaceutically-acceptable salt thereof, the weight ratio of active ingredient to carrier will normally be in the range from about 1:6 to about 2:1 and preferably from about 1:4 to about 1:1. However, in any given case, the ratio chosen will depend on such factors as the solubility of the active component, the dosage contemplated and the precise route of administration.

For oral use of a neuroleptic agent of this invention, the compound can be administered, for example, in the form of tablets or capsules or as an aqueous solution or suspension. In the case of tablets for oral use, carriers which can be used include lactose and corn starch, and lubricating agents such as magnesium stearate can be added. For oral administration in capsule form, useful diluents are lactose and dried corn starch. When aqueous suspensions are required for oral use, the active ingredient can be combined with emulsifying and suspending agents. If desired, certain sweetening and/or or flavoring agents can be added. For intramuscular and intravenous use, sterile solutions of the active ingredient can be prepared and the pH of the solutions should be suitably adjusted and buffered. For intravenous use the total concentration of solutes should be controlled to render the preparation isotonic.

When a neuroleptic agent of this invention is to be used in a human subject to treat a psychotic disorder, the daily dosage will normally be determined by the prescribing physician. Moreover, the dosage will vary according to the age, weight and response of the individual patient as well as the severity of the patient's symptoms. However, in most instances an effective amount for treating a psychotic disorder will be a daily dosage in the range from about 3 mg to about 600 mg and preferably from about 30 mg to about 60 mg in single or divided doses, orally or parenterally. In some instances, it may be necessary to use dosages outside these limits.

The present invention is illustrated by the following examples, but is not limited to the details thereof.

EXAMPLE 1

5-(2-(4-(6-Fluoro-1,2-benzisoxazol-3-yl)-1-piperidinyl)ethyl)oxindole

Under $N_2$ a mixture of 4-(6-fluoro-1,2-benzisoxazol-3-yl)piperidine V (2.0 g, 9.08 mmol), 5-(2-chloroethyl)oxindole (0.95 g, 10 mmol), $Na_2CO_3$ (1.06 g, 10 mmol) and KI (1.0 g, 6.0 mmol) in 45 ml dry DMF was heated at 90° C. for 72 hours. The reaction mixture was then poured over 150 ml ice/water, stirred, and filtered to give 3.04 g of brown solids. Chromatography on silica gel (230–400 mesh), eluting with 95% EtOAc: 5% triethylamine provided clean product, 0.645 g (19%), light brown solid, m.p. 199°–204° C. Analysis for $C_{22}H_{22}FN_3O_2 \cdot 0.5H_2O$: C 68.03, H 5.97, N 10.82. Found: C 67.94, H 5.57, N 10.81; MS(%): 379 (1, p+), 253 (4), 234 (32), 233 (100). NMR (300 MHz, $CDCl_3$, delta), 2.0–2.4 (m, 6H), 2.65 (m, 2H), 2.8 (m, 2H), 3.1–3.2 (m,3H), 3.5 (s, 2H), 6.75 (d, 1H), 7.1 (m, 3H), 7.2 (s, 1H), 7.7 (m, H), 8.25 (br s, 1H).

EXAMPLES 2–5

By a similar procedure the following were also prepared:

2.

1,3-dimethyl-5-(2-(4-(6-fluoro-1,2-benzisoxazol-3-yl)piperidinyl)ethyl)oxindole hydrochloride hydrate 35%, m.p. 104° C. (dec.). Analysis for $C_{24}H_{26}FN_3O_2 \cdot HCl \cdot 1.5H_2O$: C 61.21, H 6.42, N 8.92. Found: C 61.28, H 6.40, N 8.64. MS(%): 407 (3,p+), 233 (100).

3.

3,3-dimethyl-5-(2-(4-(6-fluoro-1,2-benzisoxazol-3-yl)piperidinyl)ethyl)oxindole hydrochloride quarterhydrate 21%, m.p. 268° C. (dec.). Analysis for $C_{24}H_{26}FN_3O_2 \cdot HCl \cdot 0.25 H_2O$: C 64.28, H 6.18, N 9.37. Found: C 64.33, H 5.79, N 9.10. MS(%): 407 (3, p+), 269(4), 233 (100).

4.

6-(2-(4-(6-fluoro-1,2-benzisoxazol-3-yl)piperidinyl)ethyl)-1,2,3,4-tetrahydro-2(1H)-quinolinone 50%, m.p. 193°-195° C. Analysis for $C_{23}H_{24}FN_3O_2 \cdot 0.5H_2O$: C 68.64, H 6.26, N 10.44. Found: C 68.65, H 5.94, N 10.13; MS(%): 393 (2, p+), 233(100).

5.

1-(4-(4-(2-methylthiazol-4-yl)phenyl)butyl)-4-(6-fluoro-1,2-benzisoxazol-3-yl)piperidine dihydrochloride hemihydrate 34%, m.p. 188°-189° C. Analysis for $C_{26}H_{28}FN_3OS \cdot 2HCl \cdot 0.5H_2O$: C 58.75, H 5.88, N 7.91. Found: C 58.40, H 5.96, N 7.80; MS(%): 451 (6), 450 (20), 449 (52,p+), 311 (33), 233 (100).

PREPARATION A 4-(6-Fluoro-1,2-benzisoxazol-3-yl)-piperidine hydrochloride (V)

N-Acetyl isonipecotoyl chloride (70.0 g, 0.369 mol) was added over a 20 minute period to a vigorously stirred suspension of AlCl$_3$ (98 g, 0.735 mol) in 1,3-difluorobenzene (125 ml, 1.27 mol, Aldrich Chem. Co.) at 25° C. The mixture was then refluxed, under N$_2$ for 4.5 hours, cooled to 25° C., and poured over 300 ml of ice/water. The layers were separated, the aqueous layer was extracted (2×100 ml CH$_2$Cl$_2$) and combined with the organic layer and dried with MgSO$_4$. Concentration in vacuo gave 4-(2,4-difluorobenzoyl)-1-acetyl-piperidine (II) as a white solid (81 g, 82%), m.p. 94°-96° C.

The preceding ketone (40 g, 0.15 mol) was added to a mixture of 125 ml concentrated HCl and 125 ml acetic acid and refluxed for 16 hours, cooled, and concentrated in vacuo. The white residue was triturated with hot isopropanol, filtered, washed with Et$_2$O and dried to give 32.3 g (83%) of 4-(2,4-difluorobenzoyl)-piperidine hydrochloride (III), m.p. 215°-216° C.

The above material (32 g, 0.122 mol), hydroxylamine.HCl (8.5 g, 0.122 mol) and triethylamine (24.8 g, 0.224mol) in EtOH (250 ml) was refluxed under N$_2$ for 4 hours, cooled and filtered to provide the oxime (IV), 27.44 g (93%), m.p. 246°-252° C.

Crude IV in 300 ml of 50% aqueous NaOH was refluxed for 4 hours, cooled and extracted with toluene (3-100 ml). The organic extracts were washed with saturated NaCl, dried (MgSO$_4$) and concentrated to a yellow residue. Chromatography on silica gel (230-400 mesh) eluting with 19 CH$_2$Cl$_2$:1 CH$_3$OH:0.1 NH$_4$OH produced the title product (V), converted to its hydrochloride with HCl gas in Et$_2$O, 5.0 g (17%), m.p. 295° C. (dec.).

PREPARATION B, C

The substituted 5-(2-chloroethyl)oxindoles used in Examples 2 and 3 were prepared in an analagous fashion to preparation D from the appropriate starting materials (i.e., 1,3-dimethyloxindole and 3,3-dimethyloxindole, respectively).

PREPARATION D 6-(2-chloroethyl)-1,2,3,4-tetrahydro-2(1H)-quinolinone

Under N$_2$ a mixture of chloroacetyl chloride 5.2 ml, 0.065 mol) and AlCl$_3$ (41.4 g, 0.31 mol) in 200 ml CS$_2$ was stirred mechanically while 1,2,3,4-tetrahydro-2(1H)-quinolinone (7.36 g, 0.05 mol, prepared according to the method of JACS, 1944, 66, 1442) was added over a 5 minute period. The mixture was refluxed for 2 hours and another 20 ml chloroacetyl chloride was added. After a further 3 hours at reflux, the dark green reaction mixture was cooled to 25° C., the CS$_2$ was decanted, and the residue was slowly decomposed by pouring slowly over 500 g ice. (NOTE: vigorous evolution of HCl!) The resulting solids were filtered, washed well with H$_2$O and air dried to give 10.7 g (96%) of crude 6-chloroacetyl-1,2,3,4-tetrahydro-2(1H)-quinolinone, m.p. 215-218° C.; MS(%): 233 (9, p+), 174 (100).

Under N$_2$, the above intermediate (6.71 g, 0.03 mol) in trifluoroacetic acid (23 ml, 0.3 mol) was treated dropwise with triethylsilane (11 ml, 0.069 mol) while maintaining an internal temperature below 25° C. After 72 hours at 25° C. the brown solution was poured over 200 ml ice/water and stirred to produce a tan solid which was further washed with water and dried to give the title product, 5.42 g (86%), m.p. 148-152° C. (dec.); MS(%): 211, 209 (34, p+), 160(100). NMR (d$_6$-DMSO, 300MHz, delta), 2.0-2.3 (m, 2H), 2.4-2.75 (m, 4H), 3.4 (t, 2H), 6.4 (d, 1H), 6.6-6.8 (m, 2H), 9.7 (br s, 1H).

PREPARATION E

The chlorobutyl thiazolyl substituted phenyl used in Example 5 was prepared according to the following method and as described in E.P. Application 279,598. 4-Chlorobutylacetophenone: To a 250 ml round-bottomed flask were added 5.0 g (29.65 mmol) 1-chloro-4-phenylbutane and 10 ml 1,2-dichloroethane. To the stirred solution was added a solution of 4.35 g (32.62 mmol) aluminum chloride and 4.22 ml (59.31 mmol) acetyl chloride in 50 ml 1,2-dichloroethane. The solution evolved HCl as it was stirred at room temperature for 1 hour. It was then poured into water, the layers separated, and the organic layer washed with 1N HCl, aqueous sodium bicarbonate solution, brine, dried over sodium sulfate, and evaporated to an oil, 6.7 g (>100%). NMR (delta, CDCl$_3$) 1.76 (m, 4H), ~2.5 (s, 3H), 3.50 (m, 2H), 7.2 and 7.85 (m, 4H). IR cm$^{-1}$, neat): 1678 (C=O).

4-(4-Chlorobutyl)phenyl-2-methylthiazole hydrobromide: The above oil was added to a 100 ml round-bottomed flask equipped with N$_2$ inlet along with 15 ml acetic acid. Bromine (1.53 ml, 29.65 mmol) was added dropwise and the solution stirred at room temperature for 15 minutes (decolorizes in about 7 minutes). The solution was taken up in ethyl acetate (careful—the bromide is a potent lachrymator), washed with water, aqueous sodium bicarbonate solution, brine, dried over sodium sulfate, and evaporated to an oil, 8.9 g (about 100% yield).

The oil was dissolved in 70 ml acetone, treated with 2.23 g (29.65 mmol) thioacetamide (which gives a precipitate, which, however, is not product) and refluxed 15 hours. The reaction was cooled, evaporated to 10 ml volume to afford a precipitate, filtered, the precipitate washed with 10 ml acetone, then washed thoroughly with ether and dried to a white solid, mp 128-129° C., 6.8 g (66.2%). NMR (delta, DMSO-d$_6$) 1.85 (m, 4H), 2.5 (m, 2H), 2.77 (s, 3H), 3.5 (m, 2H), 7.2 and 7.8 (m; 4H), 7.92 (s, 1H). IR (cm$^{-1}$, DMSO): 1620. MS (%): 265/267 (parent, 7.5/3.7), 189 (17), 188 (100), 147 (39), 115 (11), 82 (10).

I claim:

1. A 4-(1,2-Benzisoxazolyl)-piperidine compound of the formula

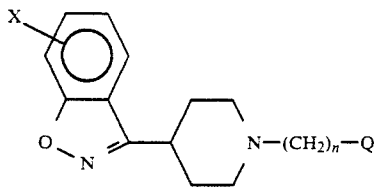

Formula I and the pharmaceutically acceptable base salts thereof; wherein

X is H, halo, $C_1$-$C_4$ alkyl, $C_1$-$C_4$ alkoxyl or $CF_3$;

n is 2, 3 or 4; and

Q is

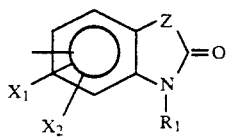

wherein Z is $CR_2R_3$, $R_1$, $R_2$ and $R_3$, are H, or $C_1$-$C_4$ alkyl; and $X_1$ and $X_2$ are H or halo.

2. A compound according to claim 1 wherein Z is $CR_2R_3$.

3. A compound according to claim 2 wherein n is 2 and X is H or halo.

4. A compound according to claim 3 wherein X is halo, $X_1$ and $X_2$ are H, and $R_1$, $R_2$, $R_3$.

5. A compound according to claim 1 said compound being 5-(2-(4-(6-Fluoro-1,2-benzisoxazol-3-yl)-1-piperidinyl)ethyloxindole, 1,3-dimethyl-5-(2-(4-(6-fluoro-1,2-benzisoxazol-3-yl)-piperidinylethyl)-oxindole, 3,3-dimethyl-5-(2-(4-(6-fluoro-1,2-benzisoxazol-3-yl)-piperidinyl)ethyl)-oxindole.

6. A pharmaceutical composition for the treatment or prevention of psychosis and anxiety, which comprises a compound according to claim 1 in a pharmaceutically acceptable carrier.

7. A method for the treatment or prevention of psychosis or anxiety, comprising administering to a person in need of said treatment or prevention a compound according to claim 1 in an amount effective to treat or prevent psychosis or anxiety.

* * * * *